(12) United States Patent
Laforest et al.

(10) Patent No.: US 7,829,312 B2
(45) Date of Patent: Nov. 9, 2010

(54) METHODS FOR RELATIVE QUANTIFICATION OF SPECIFIC NUCLEIC ACID SEQUENCES

(75) Inventors: Martin Laforest, Quebec (CA); Nathalie Hubert, Quebec (CA); Benoît S. Landry, Quebec (CA)

(73) Assignee: DNA Landmarks, Inc., Quebec (CA)

( * ) Notice: Subject to any disclaimer, the term of this patent is extended or adjusted under 35 U.S.C. 154(b) by 636 days.

(21) Appl. No.: 10/552,155

(22) PCT Filed: Apr. 11, 2003

(86) PCT No.: PCT/CA03/00547

§ 371 (c)(1), (2), (4) Date: Jan. 12, 2006

(87) PCT Pub. No.: WO2004/090160

PCT Pub. Date: Oct. 21, 2004

(65) Prior Publication Data

US 2007/0148646 A1 Jun. 28, 2007

(51) Int. Cl.
*C12P 19/34* (2006.01)

(52) U.S. Cl. .................................... 435/91.2; 435/91.21

(58) Field of Classification Search ................ 435/91.2
See application file for complete search history.

(56) References Cited

U.S. PATENT DOCUMENTS

| 5,705,365 A | * | 1/1998 | Ryder et al. | ............... 435/91.1 |
| 5,840,487 A | * | 11/1998 | Nadeau et al. | ................. 435/6 |
| 5,858,658 A | * | 1/1999 | Haemmerle et al. | ............ 435/6 |
| 6,210,891 B1 | | 4/2001 | Nyren et al. | |
| 2003/0054386 A1 | * | 3/2003 | Antonarakis et al. | ............ 435/6 |
| 2005/0089862 A1 | * | 4/2005 | Therianos et al. | .............. 435/6 |

FOREIGN PATENT DOCUMENTS

| WO | 00/63437 | 10/2000 |
| WO | WO 00/63437 A3 | 10/2000 |
| WO | 01/42496 | 6/2001 |
| WO | 02/20837 | 3/2002 |
| WO | WO 02/20837 A2 | 3/2002 |

OTHER PUBLICATIONS

Pourmand et al. Multiplex Pyrosequencing. Nucleic acids research, vol. 30, No. 7, pp. e31/1-5, 2002.*
Ronaghi et al. Journal of Chromoatography B, vol. 782, pp. 62-72, 2002.*
Alderborn, Anders, et al., "Determination of Single-Nucleotide Polymorphisms by Real-Time Pyrophosphate DNA Sequencing," Genome Research, 10:1249-1258 (2000).
Bernard, Philip S., et al., "Real-Time PCR Technology for Cancer Diagnostics," Clinical Chemistry, 48(8):1178-1185 (2002).
Pielberg, Gerli, et al., "Unexpectedly High Allelic Diversity at the KIT Locus Causing Dominant White Color in the Domestic Pig," Genetics, 160:305-311 (2002).
Pielberg, Gerli, et al., "A Sensitive Method for Detecting Variation in Copy Numbers of Duplicated Genes," Genome Research, 13:2171-2177 (2003).
Qiu, Ping, et al., "Quantification of Single Nucleotide Polymorphisms by Automated DNA Sequencing," Biochemical and Biophysical Research Communications, 309:331-338 (2003).
Reis, Patricia P., et al., "Quantitative Real-Time PCR Identifies a Critical Region of Deletion on 22q13 Related to Prognosis in Oral Cancer," Oncogene, 21:6480-6487 (2002).
Ronaghi, Mostafa, "Pyrosequencing Sheds Light on DNA Sequencing," Genome Research, 11:3-11 (2001).
Harris et al., Science, 320(5872):106-109 (2008). "Single Molecule DNA Sequencing of a Viral Genome."

* cited by examiner

*Primary Examiner*—Gary Benzion
*Assistant Examiner*—Cynthia B Wilder
(74) *Attorney, Agent, or Firm*—Nixon Peabody LLP (57) ABSTRACT

This invention relates generally to a method for quantifying the number of occurrences of a specific nucleic acid sequence within a nucleic acid sample in order to circumvent the shortcomings of the methods currently available and to provide reliable quantification of a specific nucleic acid sequence within a nucleic acid sample. The present invention provides a method of assessing an amount of a known target nucleic acid sequence in a sample comprising co-amplifying said target nucleic acid sequence and a known amount of a known control nucleic acid sequence to produce respective target and control amplicons, wherein said control nucleic acid sequence is different than said target nucleic acid sequence; and determining relative amounts of said respective amplicons by determining relative quantities of a primer extension reaction using each of said respective amplicons as a template.

35 Claims, 4 Drawing Sheets

| | | | | |
|---|---|---|---|---|
| 1 | GAGCTAAGCA | CATACGTCAG | AAACCATTAT | TGCGCGTTCA | AAAGTCGCCT |
| 51 | AAGGTCACTA | TCAGCTAGCA | AATATTTCTT | GTCAAAAATG | CTCCACTGAC |
| 101 | GTTCCATAAA | TTCCCCTCGG | TATCCAATTA | GAGTCTCATA | TTCACTCTCA |
| 151 | ATCCAAATAA | TCTGCACCGG | ATCTGGATCG | TTTCGCATGA | TTGAACAAGA |
| 201 | TGGATTGCAC | GCAGGTTCTC | CGGCCGCTTG | GGTGGAGAGG | CTATTCGGCT |
| 251 | ATGACTGGGC | ACAACAGACA | ATCGGCTGCT | CTGATGCCGC | CGTGTTCCGG |
| 301 | CTGTCAGCGC | AGGGCGCCC | GGTTCTTTTT | GTCAAGACCG | ACCTGTCCGG |
| 351 | TGCCCTGAAT | GAACTGCAGG | ACGAGGCAGC | GCGGCTATCG | TGGCTGGCCA |
| 401 | CGACGGGCGT | TCCTTGCGCA | GCTGTGCTCG | ACGTTGTCAC | TGAAGCGGGA |
| 451 | AGGGACTGGC | TGCTATTGGG | CGAAGTGCCG | GGGCAGGATC | TCCTGTCATC |
| 501 | TCACCTTGCT | *CCTGCCGAGA* | *AAGTATC*CAT | CATGGCTGAT | GCAATGCGGC |
| 551 | GGCTGCATAC | GCTTGATCCG | GCTACCTGCC | CATTCGACCA | CCAAGCGAAA |
| 601 | CATCGCATCG | AGCGAGCACG | TACTCGGATG | GAAGCCGGTC | TTGTCGATCA |
| 651 | GGATGATCTG | GACGAAGAGC | ATCAGGGGCT | CGCGCCAGCC | GAACTGTTCG |
| 701 | CCAGGCTCAA | GGCGCGCATG | CCCGACGGCG | ATGATCTCGT | CGTGACCCAT |
| 751 | GGCGATGCCT | GCTTGCCGAA | TATCATGGTG | GAAAATGGCC | GCTTTTCTGG |
| 801 | ATTCATCGAC | TGTGGCCGGC | TGGGTGTGGC | GGACCGCTAT | CAGGACATAG |
| 851 | CGTTGGCTAC | CCGTGATATT | GCTGAAGAGC | TTGGCGGCGA | ATGGGCTGAC |
| 901 | CGCTTCCTCG | TGCTTTACGG | TATCGCCGCT | CCCGATTCGC | AGCGCATCGC |
| 951 | CTTCTATCGC | CTTCTTGACG | AGTTCTTCTG | AGCGGGACTC | TGGGGTTCGA |
| 1001 | AATGACCGAC | CAAGCGACGC | CCAACCTGCC | ATCACGAGAT | TTCGATTCCA |
| 1051 | CCGCCGCCTT | CTATGAAAGG | TTGGGCTTCG | GAATCGTTTT | CCGGGACGCC |
| 1101 | GGCTGGATGA | TCCTCCAGCG | CGGGGATCTC | ATGCTGGAGT | TCTTCGCCCA |
| 1151 | CGGGATCTCT | GCGGAACAGG | CGGTCGAAGG | TGCCGATATC | ATTACGACAG |
| 1201 | CAACGGCCGA | CAAGCACAAC | GCCACGATCC | TGAGCGACAA | TATGATCGGG |
| 1251 | CCCGGCGTCC | ACATCAACGG | CGTCGGCGGC | GACTGCCCAG | GCAAGACCGA |
| 1301 | GATGCACCGC | GATATCTTGC | TGCGTTCGGA | TATTTCGTG | GAGTTCCCGC |
| 1351 | CACAGACCCG | GATGATCCCC | GATCGTTCAA | ACATTTGGCA | ATAAAGTTTC |
| 1401 | TTAAGATTGA | ATCCTGTTGC | CGGTCTTGCG | ATGATTATCA | TATAATTTCT |
| 1451 | GTTGAATTAC | GTTAAGCATG | TAATAATTAA | CATGTAATGC | ATGACGTTAT |
| 1501 | TTATGAGATG | GGTTTTTATG | ATTAGAGTCC | CGCAATTATA | CATTTAATAC |
| 1551 | GCGATAGAAA | ACAAAATATA | GCGCGCAAAC | TAGGATAAAT | TATCGCGCGC |

Figure 1

```
1    GACATACCTA GGATCGTTCA AGAAGCTTTC TTTCTAGCTA CTTCCGGTAG
51   ACCCGGACCG GTTTTGGTTG ATGTTCCTAA GGATATTCAG CAGCAGCTTG
101  CGATTCCTAA CTGGGATCAA CCTATGCGCT TACCTGGCTA CATGTCTAGG
151  TTGCCTCAGC CTCCGGAAGT TTCTCAGTTA GGTCAGATCG TTAGGTTGAT
201  CTCGGAGTCT AAGAGGCCTG TTTTGTACGT TGGTGGTGGA AGCTTGAACT
251  CGAGTGAAGA ACTGGGGAGA TTTGTCGAGC TTACTGGGAT CCCCGTTGCG
301  AGTACTTTGA TGGGGCTTGG CTCTTATCCT TGTAACGATG AGTTGTCCCT
351  GCAGATGCTT GGCATGCACG GGACTGTGTA TGCTAACTAC GCTGTGGAGC
401  ATAGTGATTT GTTGCTGGCG TTTGGTGTTA GGTTTGATGA CCGTGTCACG
451  GGAAAGCTCG AGGCTTTCGC TAGCAGGGCT AAAATTGTGC ACATAGACAT
501  TGATTCTGCT GAGATTGGGA AGAATAAGAC ACCTCACGTG TCTGTGTGTG
551  GTGATGTAAA GCTGGCTTTG CAAGGGATGA ACAAGGTTCT TGAGAACCGG
601  GCGGAGGAGC TCAAGCTTGA TTTCGGTGTT TGGAGGAGTG AGTTGAGCGA
651  GCAGAAACAG AAGTTCCCTT TGAGCTTCAA AACGTTTGGA GAAGCCATTC
701  CTCCGCAGTA CGCGATTCAG ATCCTCGACG AGCTAACCGA AGGGAAGGCA
751  ATTATCAGTA CTGGTGTTGG ACAGCATCAG ATGTGGGCGG CGCAGTTTTA
801  CAAGTACAGG AAGCCGAGAC AGTGGCTGTC GTCATCAGGC CTCGGAGCTA
851  TGGGTTTTGG ACTTCCTGCT GCGATTGGAG CGTCTGTGGC GAACCCTGAT
901  GCGATTGTTG TGGATATTGA CGGTGATGGA AGCTTCATAA TGAACGTTCA
951  AGAGCTGGCC ACAATCCGTG TAGAGAATCT TCCTGTGAAG ATACTCTTGT
1001 TAAACAACCA GCATCTTGGG ATGGTCATGC AATGGGAAGA TCGGTTCTAC
1051 AAAGCTAACA GAGCTCACAC TTATCTCGGG GACCCGGCAA GGGAGAACGA
1101 GATCTTCCCT AACATGCTGC AGTTTGCAGG AGCTTGCGGG ATTCCAGCTG
1151 CGAGAGTGAC GAAGAAAGAA GAACTCCGAG AAGCTATTCA GACAATGCTG
1201 GATACACCAG GACCATACCT GTTGGATGTG ATATGTCCGC ACCAAGAACA
1251 TGTGTTACCG ATGATCCCAA GTGGTGGCAC TTTCAAAGAT GTAATAACAG
1301 AAGGGGATGG TCGCACTAAG TACTGAGAGA TGAAGCTGGT GATCGATCAT
1351 ATGGTAAAAG ACTTAGTTTC AGTTCCAGT TTCTTTTGTG TGGTAATTTG
1401 GGTTTGTCAG TTGTTGTACT ACTTTTGGTT GTTCCCAGAC GTACTCGCTG
1451 TTGTTGTTTT GTTTCCTTTT TCTTTTATAT ATAAATAAAC TGCTTGGGTT
1501 TTTTTTCATA TGTTTGGGAC TCAATGCAAG GAATGCTACT AGACTGCGAT
1551 TATCTACTAA TCTTGCTAGG AAAT
```

METHODS FOR RELATIVE QUANTIFICATION OF SPECIFIC NUCLEIC ACID SEQUENCES

CROSS-REFERENCE TO RELATED APPLICATIONS

This application is a 371 National Phase Entry Application of co-pending International Application PCT/CA2003/000547, filed Apr. 11, 2003, which designated the U.S.; the contents of which are herewith incorporated by reference in their entirety.

BACKGROUND OF THE INVENTION (a) Field of the Invention

This invention relates generally to a novel method for quantifying the number of occurrences of a specific nucleic acid sequence within a nucleic acid sample in order to circumvent the shortcomings of the methods currently available and to provide reliable quantification of a specific nucleic acid sequence within a nucleic acid sample.

(b) Description of Prior Art

DNA Quantification

Biological processes are governed, in part, by the presence of specific DNA sequences present in the genome of living organisms. Their relative quantities or respective expression levels will contribute to define cellular functions and to determine the phenotypical traits of the organism.

Considerable effort has been devoted to the development of techniques for quantifying the number of times a particular sequence occurs in a genome. One such technique is Southern hybridization (Southern, E. M., 1975, J. Mol. Biol., 98: 503-517). Briefly, DNA extracts are enzymatically digested, resolved by gel electrophoresis, transferred onto a solid support (nitrocellulose or nylon membranes) and probed with labeled poly-nucleic acids. The results show a number of bands representing restriction fragments onto which the labeled probe hybridized. The number and/or intensity of bands can be used to determine the number of copies of the targeted DNA fragment per haploid genome. This technique has the disadvantage of being time consuming and poorly adaptable to a high-throughput production environment. Also, if the labeled probe hybridizes to two restriction fragment of roughly the same size, the resulting band will have a higher intensity the other bands, if present. Therefore, in such cases, the intensities of the bands will have to be determined by other means in order to get good estimates of the number of copies of the target sequence.

Copy number determination can also be achieved by the polymerase chain reaction technique (Mullis, K., Faloona, F., Scharf, S., Saiki, R., Horn, G. & Erlich, H., 1986, Cold Spring Harbor Symp. Quant. Biol., 51: 263-273). After amplification, the PCR products are resolved onto agarose gels and visualized using DNA-specific fluorescent dyes such as ethidium bromide. The DNA-dye complex fluorescent intensity of the target DNA sequence is then compared on the agarose gel to the intensity obtained with control DNA of known concentrations. Also, the PCR amplification can be designed in such a way that two PCR products are amplified in the same reaction tube (duplex PCR). One PCR product will be specific to the target sequence and the other one will serve as a control and is constant between the two samples. The DNA-dye complex fluorescent intensity for the target sequence is then compared to the intensity obtained with the control PCR product. In both cases, this technique will produce more qualitative than quantitative estimates of the actual initial number of copy of the target sequence.

Variants of the polymerase chain reaction can be used to determine the initial number of copies of a specific target sequence. Competitive PCR is based on the principle that if two DNA fragments sharing oligonucleotide binding sites are amplified in a duplex PCR reaction, they will compete for the availability of primers. After amplification, the relative quantity of the two amplicons will be used to determine the starting number of copies for each amplicon. This technique requires that a competitor DNA be added to the genomic (sample) DNA extracts in different concentrations, and therefore has no endogenous control. It also requires that the competitor DNA sequence is different from the target DNA sequence, in most cases in length, to make it possible to distinguish it from the DNA fragment under investigation. It is then possible to determine, by gel electrophoresis for example, with which concentration of competitor DNA the amplification products were amplified in comparable amounts. This technique also requires that the concentrations of the DNA extracts be standardized prior to these quantifications in order to make comparisons between samples possible.

Real-time PCR is a method that measures amplicon quantities during the PCR amplification. This is generally achieved by adding one or two labeled oligonucleotides bearing a fluorochrome and a quencher to the PCR cocktail, (example: TaqMan assay). Fluorescence is monitored throughout the amplification and is emitted only if the two labels are not in close vicinity to each other when hybridized to one strand of the amplicon. By using fluorochromes emitting at different wavelengths linked to oligonucleotides specific to more than one amplicon, it is possible to monitor different amplicon quantities in a single tube. This allows for the possibility of amplifying an endogenous control and achieving reliable quantification of the target sequence. Real-Time PCR is particularly useful when a wide range of resolution is needed (e.g. 10 vs. 10,000 copies), but is limited in resolution when differentiating discrete variations, e.g. two, three, four or five fold more copies in one sample as compared to another one.

Potential Applications of DNA Quantification

In the process of creating genetically modified organisms (GMO), the gene conferring the novel trait is transferred into the genome of the target cells. These transformed organisms have to go through a registration process before they can be released for commercial use. For this purpose, it is necessary to select the transformants in which a single integration event took place. If the GMOs were created in order to elucidate the function of a gene or its phenotypical effects, results drawn will be more conclusive if the transgene is present only once in the genome of the transformed organism and expressed in a similar fashion as it is in its endogenous location in the source organism.

Some genes have redundant functions, meaning that two or more genes, located in separate locations in the genome, might have identical functions. The number of such paralogous genes could be determined with techniques described herein. In addition, these techniques could be used to determine if the copy number of one or more of the cell's chromosomes, or parts of chromosomes, is abnormal. For example, when cells are grown in culture, chromosomal aberrations, such as the duplication or loss of chromosomes or parts of chromosomes can occur. Such abnormalities can also occur after treatment of with mutagens.

Certain diseases are associated with abnormal ploidy. Ploidy refers to the number of copies of each individual chromosome in a cell; for most non-reproductive cells in animals and plants, this number is two (the diploid chromosome number). Under certain conditions, in some types of human tumor cells for example, this number may be greater than two for some or all chromosomes, suggesting that genetic mechanisms that maintain chromosome copy number have been disrupted. Such disruptions can be seen in prostate, ovarian and breast cancer. Studies have shown that patients with diploid cancers (having normal DNA content in cancer cells) have longer cancer-free intervals and survival than those with non-diploid cancers. Diploid tumors are also more responsive to hormonal therapy.

Ploidy counts can sometimes be used to identify specific tissues, for example, in plants. The endosperm of seeds is triploid and other tissues are diploid. Anther culture is a method for producing haploid plants that can be used for the development of double haploid populations. There have been reports of ploidy variations in anther culture of barley (Sunderland, N. (1980) In: The Plant Genome, Proc. $2^{nd}$ Haploid Symp. John Innes Inst. Norwich, pp 171-183) and unexpected ploidy variation among progeny plants in wheat, due to gametoclonal and somoclonal variations (Baenziger et al. (1989) Plant Breeding 103:53-56).

RNA Quantification

Considerable efforts have also been made to develop techniques to quantify relative amounts of RNA in extracts in order to estimate the level at which a gene is transcribed. One method for detecting the expression of a gene is Northern blotting. The principle of this technique is basically the same as for Southern blotting; purified RNA is resolved on an agarose gel in denaturing conditions, transferred onto a solid support and probed with a labeled nucleic acid sequence. The intensity of the signal corresponding to the probe hybridized to the target sequence will reflect expression level. A relative estimation of the level of expression can be obtained by comparing the intensity of the band between two RNA extracts that have been normalized by a second probe that hybridizes to an RNA that is expressed at the same level in the two extracts. When a small part of the RNA is degraded, the bands produced by the labeled probes are of unequal sizes and smeared, depending on the level of degradation. Calculating the intensity of the probe's signal on bands of different sizes will produce only a qualitative estimate, not reliable quantitative expression level data. Also, being based upon hybridization, this technique does not have a high enough resolution to discriminate the expression levels of highly identical genes. Finally, the technique is lengthy and labor intensive.

The newly developed micro-array or DNA-chip technology can also be used to monitor expression levels of genes. Polynucleotide molecules (oligonucleotides, cDNA or genomic sequences) are deposited on a solid support (glass slide, nylon or nitrocellulose paper) as homogenous dots (one dot contains polynucleotides that all share the same sequence). They are then probed with complex mixtures of labeled cDNAs or RNA. The probes and their complementary sequences deposited on the solid support hybridize and the relative quantification of expression levels of the genes can be determined by measuring the quantity of labeled probes specific to a homogenous spot. As it is the case for Northern hybridization, this technique does not have a high enough resolution to discriminate the expression levels of highly identical genes.

RNA extracts can also be treated with an enzyme called reverse transcriptase to generate corresponding DNA sequences. After such treatment, copy number or expression level analyses will be performed as it is done with DNA extracts.

It would be highly desirable to be provided with a novel method for quantifying the number of occurrences of a specific nucleic acid sequence within a nucleic acid sample in order to circumvent the shortcomings of the methods currently available and to provide reliable quantification of a specific nucleic acid sequence within a nucleic acid sample.

SUMMARY OF THE INVENTION

Surprisingly, and in accordance with the present invention, one aim of the present invention is to provide a novel method for quantifying the number of occurrences of a specific nucleic acid sequence within a nucleic acid sample in order to circumvent the shortcomings of the methods currently available.

In accordance with the present invention there is provided a method of assessing an amount of a known target nucleic acid sequence in a sample comprising co-amplifying the target nucleic acid sequence and a known amount of a known control nucleic acid sequence to produce respective target and control amplicons, wherein the control nucleic acid sequence is different than the target nucleic acid sequence, and determining relative amounts of the respective amplicons by determining relative quantities of a primer extension reaction using each of the respective amplicons as a template, wherein the primer extension reaction is performed using a sequential dispensation order of individual nucleotides, such that primer extension reactions of the respective target and control amplicons are performed sequentially of each other, and wherein determining relative quantities of a primer extension reaction comprises comparing a quantity of nucleotides incorporated during the primer extension reaction for the target amplicon with a quantity of nucleotides incorporated during the primer extension reaction for the control amplicon, wherein relative amounts of the respective amplicons are proportional to relative quantities of nucleotides incorporated during the primer extension reactions and the amount of the target nucleic acid sequence in the sample is proportional thereto.

A preferred control nucleic acid of the present invention is an endogenous or exogenous nucleic acid.

In a preferred method of the present invention the primer extension reaction is performed using identical primers for the respective target and control amplicons.

In preferred method of the present invention the primer extension reaction is performed using a different template-specific primer for the respective target and control amplicons.

In a preferred method of the present invention the primer extension reaction is detected by detecting pyrophosphate (PPi) release, preferably luminometrically or enzymatically using the enzyme luciferase as a PPi-detection enzyme.

In a preferred method of the present invention in the primer extension reaction; an α-thio analogue of an adenine nucleotide is used.

In a preferred method of the present invention the target nucleic acid and control nucleic acid are co-amplified using amplification primers which are immobilized or carry means for immobilization.

In a preferred method of the present invention more than one different control nucleic acid is used.

In a preferred method of the present invention different amounts of each different control nucleic acid are used.

In a preferred method of the present invention multiple primer extension reactions are performed on each of the respective target or control amplicons.

In a preferred method of the present invention each primer extension reaction yields an extension product of different length or sequence.

In a preferred method of the present invention the target nucleic acid is selected from the group consisting of a gene or a fragment thereof, a T-DNA region or a fragment thereof, a vector or a fragment thereof, a plasmid or fragment thereof, a nucleic acid polymorphism and a non-coding region of a nucleic acid sequence.

Preferably the gene or fragment thereof is a gene selected from the group consisting of a disease resistance gene, an antibiotic resistance gene and a gene conferring an investigated trait.

In a preferred method of the present invention the investigated (target) nucleic acid is selected from the group consisting of neomycin phosphotransferase (NPTII) phosphinothricin acetyl transferase (PAT), hygromycin phosphotransferase (HPT), acetolactate synthase (ALS, also referred to as acetohydroxyacid synthase (AHAS)), phosphomannose isomerase (PMI), 5-enolpyruvylshikamate-3-phosphate synthase (EPSP synthase), oxalate oxidase, adenosine deaminase, dihydrofolate reductase, thymidine kinase, xanthine-guanine phosphoribosyltransferase, and blasticidin S deaminase.

In accordance with another embodiment of the present invention there is provided a method of assessing copy number of a target nucleic acid sequence in a genome of an organism comprising co-amplifying the target nucleic acid sequence and a known amount of a known control nucleic acid sequence to produce respective target and control amplicons, wherein the control nucleic acid sequence is different than the target nucleic acid sequence and determining relative amounts of the respective amplicons by determining relative quantities of a primer extension reaction using each of the respective amplicons as a template, wherein the primer extension reaction is performed using a sequential dispensation order of individual nucleotides, such that primer extension reactions of the respective target and control amplicons are performed sequentially of each other, and wherein determining relative quantities of a primer extension reaction comprises comparing a quantity of nucleotides incorporated during the primer extension reaction for the target amplicon with a quantity of nucleotides incorporated during the primer extension reaction for the control amplicon, wherein relative amounts of the respective amplicons are proportional to relative quantities of nucleotides incorporated during the primer extension reactions and copy number of the target nucleic acid sequence in the genome is proportional thereto.

In accordance with another embodiment of the present invention there is provided a method of assessing copy number of a plasmid in a cell comprising co-amplifying a target nucleic acid sequence from the plasmid and a known amount of a known control nucleic acid sequence to produce respective target and control amplicons, wherein the control nucleic acid sequence is different than the target nucleic acid sequence and determining relative amounts of the respective amplicons by determining relative quantities of a primer extension reaction using each of the respective amplicons as a template, wherein the primer extension reaction is performed using a sequential dispensation order of individual nucleotides, such that primer extension reactions of the respective target and control amplicons are performed sequentially of each other, and wherein determining relative quantities of a primer extension reaction comprises comparing a quantity of nucleotides incorporated during the primer extension reaction for the target amplicon with a quantity of nucleotides incorporated during the primer extension reaction for the control amplicon, wherein relative amounts of the respective amplicons are proportional to relative quantities of nucleotides incorporated during the primer extension reactions and the copy number of the plasmid in the cell is proportional thereto.

In accordance with another embodiment of the present invention there is provided a method of identifying an organism having a single copy of a target nucleic acid sequence comprising co-amplifying the target nucleic acid sequence and a known amount of a known control nucleic acid sequence to produce respective target and control amplicons, wherein the control nucleic acid sequence is different than the target nucleic acid sequence; determining relative amounts of the respective amplicons by determining relative quantities of a primer extension reaction using each of the respective amplicons as a template, wherein the primer extension reaction is performed using a sequential dispensation order of individual nucleotides, such that primer extension reactions of the respective target and control amplicons are performed sequentially of each other, and wherein determining relative quantities of a primer extension reaction comprises comparing a quantity of nucleotides incorporated during the primer extension reaction for the target amplicon with a quantity of nucleotides incorporated during the primer extension reaction for the control amplicon, wherein relative amounts of the respective amplicons are proportional to relative quantities of nucleotides incorporated during the primer extension reactions and the copy number of the target nucleic acid sequence is proportional thereto, and determining if the copy number of the target nucleic acid sequence is one, wherein a copy number of the target nucleic acid sequence equal to one is indicative of an organism having a single copy of the target nucleic acid sequence.

In a preferred method of the present invention the organism is a genetically modified organism.

In a preferred method of the present invention the organism is identified from a plurality of organisms.

In a preferred method of the present invention the organism is an organism selected from the group consisting of mammals, plants, birds, bacteria, fungi, and viruses.

In a preferred method of the present invention the control nucleic acid is acetohydroxyacid synthase (AHAS).

In accordance with another embodiment of the present invention there is provided a kit for use in a method of the present invention, the kit comprising a known control nucleic acid sequence of known concentration and means for detecting a primer extension reaction.

In a preferred kit of the present invention the kit further comprises one or more of the following components: an extension primer for the control nucleic acid sequence and/or the target nucleic acid sequence; a primer for amplification of the target nucleic acid; a primer for amplification of the control nucleic acid; and a polymerase enzyme for amplification of the target nucleic acid and/or the control nucleic acid and/or for primer extension.

In a preferred kit of the present invention the target nucleic acid is selected from the group consisting of neomycin phosphotransferase (NPTII) phosphinothricin acetyl transferase (PAT), hygromycin phosphotransferase (HPT), acetolactate synthase (ALS, also referred to as acetohydroxyacid synthase (AHAS)), phosphomannose isomerase (PMI), 5-enolpyruvylshikamate-3-phosphate synthase (EPSP synthase), oxalate oxidase, adenosine deaminase, dihydrofolate reductase, thymidine kinase, xanthine-guanine phosphoribosyltransferase, and blasticidin S deaminase.

In a preferred method of the present invention the target nucleic acid is a chromosome or a fragment thereof and assessing an amount of the target nucleic acid is used to determine chromosome copy number.

In a preferred method of the present invention the primer extension reaction is performed using a primer specific for NPTII and another primer specific for AHAS.

For the purpose of the present invention the following terms are defined below.

The term "genome" is intended to mean the DNA sequence content of a haploid cell of an organism.

The term "amplicon" is intended to mean a nucleic acid made using the polymerase chain reaction (PCR). Typically, the amplicon is a copy of a selected nucleic acid.

The term "transformant" is intended to mean a host organism which has had a nucleic acid fragment integrated into the genome of its germ and/or somatic cells, resulting in genetically stable inheritance of the nucleic acid fragment.

The term "transgene" is intended to mean a gene integrated into the genome of the germ and/or somatic cells of an organism in a manner that ensures its function, replication and transmission as a normal gene.

The term "paralogous" is intended to mean genes that are located in separate locations in the genome, but are similar or identical in sequence. Such genes are related by gene duplication, not speciation.

The term "ploidy" is intended to mean the number of copies of each individual chromosome in a cell.

The term "oligonucleotide" is intended to mean a polymer of a plurality of (at least 2) nucleotides covalently coupled together by phosphodiester bonds and may consist of either ribonucleotides or deoxyribonucleotides. As used herein, the term "oligonucleotide" also includes DNA or RNA sequences that contain one or more modified bases. Thus, DNA or RNA sequences with backbones modified for stability or for other reasons are "oligonucleotides" as that term is intended herein. Moreover, DNA or RNA sequences comprising unusual bases, such as inosine, or modified bases, are oligonucleotides as the term is used herein. It will be appreciated that a great variety of modifications have been made to DNA and RNA that serve many useful purposes known to those of skill in the art. The term "oligonucleotide" as it is employed herein embraces such chemically, enzymatically or metabolically modified forms of oligonucleotides.

The term "primer" is intended to mean a single-stranded oligonucleotide capable of acting as a point of initiation of template-directed DNA synthesis under appropriate conditions (i.e., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer but typically ranges from 15 to 50 nucleotides. A primer need not reflect the exact sequence of the template but must be sufficiently complementary to hybridize with a template.

The term "gene" refers to a nucleic acid fragment that expresses a specific protein, including regulatory sequences preceding (5' non-coding sequences) and following (3' non-coding sequences) the coding sequence. An "endogenous gene" refers to a native gene in its natural location in the genome of an organism.

The term "transgenic" is intended to mean an organism harboring in its genome of its germ and somatic cells a transgene that has been introduced using recombinant technology.

The term "transgene" is intended to mean a gene inserted into the genome of the germ and/or somatic cells of an organism in a manner that ensures its function, replication and transmission as a normal gene. A "transgene" can be any piece of a nucleic acid molecule (for example, DNA) which is inserted by artifice into a cell, and becomes part of the organism (integrated into the genome or maintained extrachromosomally) which develops from that cell. Such a transgene may include a gene which is partly or entirely heterologous (i.e., foreign) to the transgenic organism, or may represent a gene homologous to an endogenous gene of the organism.

The term "transformation" is intended to mean the transfer of a nucleic acid fragment into the genome of a host organism, resulting in genetically stable inheritance. Examples of methods of plant transformation include, but are not limited to, Agrobacterium-mediated transformation (De Blaere et al. (1987) Meth. Enzymol. 143:277) and particle-accelerated or "gene gun" transformation technology (Klein et al. (1987) Nature (London) 327:70-73; U.S. Pat. No. 4,945,050).

The term "ortholog" is intended to mean a gene obtained from one species that is the functional counterpart of a gene from a different species. Sequence differences among orthologs are the result of speciation.

The term "paralog" is intended to mean distinct but structurally related genes in the genome of an organism. Paralogs are believed to arise through gene duplication.

The term "homeolog" is intended to mean a gene from one species, that has a common origin and functions the same as a gene from another species.

The term "T-DNA" is intended to mean the DNA sequence that is transferred into a cell through *Agrobacterium tumefaciens* mediated transformation.

BRIEF DESCRIPTION OF THE DRAWINGS

FIG. 1 illustrates a partial sequence of the NPTII gene (Genbank accession number GI: 520486) (SEQ ID NO:1). Oligonucleotides designed for specific amplification of part of the sequence are indicated in bold. The oligonucleotide used for the primer extension reaction is indicated in bold italic.

FIG. 2 illustrates a partial sequence of the ALS1 gene (Genbank accession number GI: 17771) (SEQ ID NO:2). Oligonucleotides designed for specific amplification of part of the sequence are indicated in bold. The oligonucleotide used for the primer extension reaction is indicated in bold italic.

DETAILED DESCRIPTION OF THE INVENTION

In accordance with the present invention there is provided a novel method for quantifying the number of occurrences of a specific nucleic acid sequence within a nucleic acid sample in order to circumvent the shortcomings of the methods currently available.

The method described herein is used to quantify the relative number of copies of any given nucleic acid sequence. It allows for comparison of different nucleic acid samples and the assessment of the relative copy number of a specific sequence between these samples. These samples are generally composed of DNA but can be also composed of RNA (for example, during expression level analysis). In the latter case, DNA copies of RNA sequences in the samples must be made by using RNA-dependant DNA-polymerases. After this required step, the nucleic acid samples can be treated in the same fashion, regardless of their origin.

This invention provides techniques to reliably quantify specific nucleic acid sequences within nucleic acid samples. In one embodiment, the relative number of copies of the NPTII gene was established in transformed canola plants (*Brassica napus*, L.).

In other embodiments other target nucleic acid sequences which could be quantitated include, but are not limited to, a gene or a fragment thereof, a T-DNA region or a fragment thereof, a vector or a fragment thereof, a plasmid or fragment thereof, a nucleic acid polymorphism and non-coding regions.

Such a gene or fragment thereof could be a disease resistance gene, an antibiotic resistance gene, or any other gene conferring an investigated trait.

The first step of this invention is to identify the nucleic acid sequence to be quantitated and a nucleic acid sequence to be used as a control. The latter should be constant between samples to be compared. Oligonucleotides are then designed to specifically amplify each defined nucleic acid sequence by PCR amplification. PCR amplifications are performed using different DNA samples. The amplifications are done in duplex: this means that both sets of primers (one set specific the sequence to be quantitated and the other set specific to the control nucleic acid sequence) are combined in the same reaction tube along with template DNA. The PCR conditions are established in such a way that the plateau effect of the PCR amplification is never reached: the PCR amplification is stopped while still in its exponential phase (the plateau effect is reached when one of the reaction components becomes a limiting factor and PCR products no longer accumulate at an exponential rate). Oligonucleotides not used during elongation are removed after PCR amplification. Two new template-specific primers are designed, one specific to each amplicon, and added to the amplified samples. A primer extension reaction is performed and the relative quantity of each extension product measured. Since the relative quantity of the nucleic acid sequence to be quantitated is calculated using the control sequence, amplified from all extracts to be compared, these relative values can be compared between experiments and relative initial copy number determined.

The investigated (target) nucleic acid sequence (the nucleic acid sequence to be quantitated) could be specific to a transformation selection marker, as is the case for neomycin phosphotransferase (NPTII) in the transformation of canola. Other selection markers can also be used for the same purpose. Examples of such selection markers include, but are not limited to, phosphinothricin acetyl transferase (PAT), hygromycin phosphotransferase (HPT), acetolactate synthase (ALS, also referred to as acetohydroxyacid synthase (AHAS)), phosphomannose isomerase (PMI), 5-enolpyruvylshikamate-3-phosphate synthase (EPSP synthase), oxalate oxidase, adenosine deaminase, dihydrofolate reductase, thymidine kinase, xanthine-guanine phosphoribosyltransferase, and blasticidin S deaminase. The investigated (target) nucleic acid sequence is generally, but not limited to, a part of the vector used to create transgenic events. The list above enumerates only some selective markers which could be present in a transformation vector and used to select cells in which integrations of the vector took place, conferring a novel trait to these cells. Any parts of the transformation vector, including but not limited to the selective marker gene, promoter, non-coding sequence or passenger gene can be used to monitor the number of integrations within the host cells. The investigated (target) sequence could also be any sequence that can be amplified by standard techniques. Other examples include, but are not limited to: coding regions of genes, non-coding regions, synthetic nucleic acid molecules, ortholog, paralog or homeolog genes, duplicated endogenous sequences, transformation vectors, viral nucleic acids sequences and RNA.

For the purpose of quantification of a specific nucleic acid sequence, another sequence, or control sequence, for which the number of occurrences is the same, and known, in all the nucleic acid samples and that can serve as a reference control for relative quantification, must be identified. Examples of possible control sequences include, but are not limited to, coding regions of genes (for example, acetolactate synthase, actin, profilin, ferredoxin-dependent glutamate synthase, ribose-phosphate pyrophosphokinase, beta-ketoacyl-CoA synthase, delta-5 fatty acid desaturase) and non-coding sequences (for example, gene promoters, introns, up-stream and down stream non-coding translated regions, sequence-tag sites (STS) of known copy number and non-translated sequences of known copy number).

Specific oligonucleotide amplification primers are designed for the target sequence as well as for the identified control sequence. Using these specific primers, amplifications are performed in duplex in order to amplify both target and control amplicons in the same reaction. The amplification technique is usually the method described by Mullis et al. (Mullis, K., Faloona, F., Scharf, S., Saiki, R., Horn, G. & Erlich, H., 1986, Cold Spring Harbor Symp. Quant. Biol., 51: 263-273) called the polymerase chain reaction. It is important that the amplification not be allowed to proceed to the plateau phase since in this case the final number of PCR products at the plateau phase would not represent the initial copy number of both the targeted nucleic acid sequences or the control nucleic acid sequence. For the purpose of quantifying the initial copy number, the PCR amplification must be stopped at a stage where the oligonucleotides amplification primers are not a limiting factor, i.e. during the exponential phase of the amplification.

After amplification, specific extension primers, one for each amplicon, are designed and used in a primer extension reaction. The quantity of each primer extension reaction product is monitored using quantitative instruments such as a Pyrosequencer (Pyrosequencing Inc.). Relative quantities of the extension products are determined using the control nucleic acid as a reference allowing comparisons between different samples.

The method by which the quantity of primer extension products is determined will determine certain aspects of the procedures. For example, the standard protocol for DNA analysis using the Pyrosequencing technology requires that 45 to 50 PCR cycles are done in order to exhaust all oligonucleotides amplification primers. Should there be oligonucleotides amplification primers left, they would interfere in the later steps of Pyrosequencing and would produce unreliable data. However, after 45 to 50 PCR cycles, where amplification is no longer in exponential phase, it is unlikely that the final quantity of PCR products would represent the initial copy number of both the targeted and control nucleic acid sequences, as stated above. Stopping the PCR amplification during the exponential phase will produce samples where there are remaining oligonucleotides amplification primers that could interfere with the Pyrosequencing assay. To circumvent this problem, PCR reaction samples are treated, after cycling, to remove any oligonucleotides and single stranded DNA that could be detrimental to the outcome of the experiment. In the example described, oligonucleotides and single stranded DNA are degraded using Mung bean nuclease. Removal of excess oligonucleotides amplification primers and could also be achieved by other means like the ExoSAPit kit, exonuclease 1, purification columns (QiaQuick, MiniElute, etc.).

The present invention will be more readily understood by referring to the following examples which are given to illustrate the invention rather than to limit its scope.

Example 1

Relative Quantification of the Initial Copy Number of the Transgene NPTII in Canola Plants Materials and Methods DNA Extraction Approximately 30 g of frozen tissues are ground in 100 ml of extraction buffer (100 mM Tris, 70 mM EDTA, 9.11%(w/v) sorbitol, 0.38%(w/v) sodium metabisulfite, 2%(w/v) CTAB) and filtered with cheesecloth. The filtrate is centrifuged at 5,200 RPM for 15 min at 4° C. and the pellet resuspended in 15 ml of resuspension buffer (100 mM Tris, 70 mM EDTA, 9.11%(w/v) sorbitol, 0.38%(w/v) sodium metabisulfite, 2%(w/v) CTAB, 0.01 mg/ml RNAse). Then 15 ml of lysis buffer (200 mM Tris, 70 mM EDTA, 2 M NaCl) and 3 ml of 5%(w/v) sarkosyl is added to the tube, mixed by inverting a few times and incubated 15 min at 60° C. Following this, 18 ml of chloroform/isoamyl-alcohol(24:1) is added, mixed by inverting a few times and the mixture is then spun at 6,000 RPM for 10 min at 4° C. The aqueous phase is transferred to a fresh tube and the chloroform/isoamyl-alcohol extraction repeated a second time. The aqueous phase is transferred into a fresh tube, 20 ml of isopropanol added and nucleic acids are precipitated on ice for 1 hr. The solution is then centrifuged 15 min at 3,400 RPM and the pellet washed with 3 ml of 70% ethanol. The pellet is then left to dry for 30 min and then resuspended in 100 µl of TE.

DNA Amplification and Clean-Up

PCR amplifications are performed using HotStarTaq (Qiagen) according to the manufacturer's recommendations. In this example, single strand DNA purification was performed using streptavidin-coated magnetic beads. The same goal can be reached by other means, for example, but not limited to, by using streptavidin-coated sepharose beads. PCR products specific to the NPTII gene are amplified using oligonucleotide primers NPTII-F (5'-CAGCTGTGCTC-GACGTTGTCA-3') (SEQ ID NO:3) and NPTII-R (5'-GC-CATGGGTCACGACGAGAT-3') (SEQ ID NO:4). To amplify part of the ALS1 gene, oligonucleotide primers ALS1-F (5'-GGAAAGCTCGAGGCTTTCGCT-3') (SEQ ID NO:5) and ALS1-R (5'-GCCGCCCACATCTGATGCTGT-3') (SEQ ID NO:6) are used. The oligonucleotide primers NPTII-R and ALS1-R are modified with a biotin tag (Thermo-Hybaid) linked at their most 5'-nucleotide. The oligonucleotide primers (0.3 µM) specific to ALS1 and NPTII are used in a duplex PCR reaction with 0.4 ng of genomic DNA and the amplifications are performed on a ABI Gene-Amp PCR system 9700 for 33 cycles (1 min 94° C., 57.5° C. 30 sec and 72° C. 30 sec). The reactions are then treated with Mung Bean nuclease (2 units) as recommended by the manufacturer (Amersham Pharmacia Biotech) for 30 min at 37° C. followed by heat inactivation for 15 min at 94° C.

Primer Extension PCR for Quantitative Detection ALS1 and NPTII PCR Products Using PYROSEQUENCING™ (PSQ™96 System) Technology Primer extension reactions is performed using sequencing primers specific to ALS1 (ALS1 PT, 5'-TTTGGAGGAGT-GAGTT-3') (SEQ ID NO:7) and to NPTII (NPTIIPT, 5'-CT-GCCGAGAAAGTATC-3') (SEQ ID NO:8) on the Pyrosequencer (Pyrosequencing Inc.) as recommended by the manufacturer. Single stranded DNA is purified by affinity with streptavidin coated magnetic beads. The dispensation order of the nucleotides is CATCAGAGCGA (SEQ ID NO:9). The expected sequence for NPTII is CATCAT and since there is only one T in the dispensation order, the primer extension reaction of NPTII is stopped after five nucleotides. The expected sequence for ALS1 is GAGCGA. Since there is no G in the first five nucleotides of the dispensation order, the ALS primer extension reaction only begins when the first G is dispensed, after the primer extension reaction of NPTII has stopped. With this specific dispensation order, the two amplicons (NPTII and ALS1) are analyzed separately.

Relative Quantification of the Initial Copy Number of the Transgene NPTII

PCR amplifications are performed in duplex using NPTII- and ALS1-specific sets of primers. The standard protocol for DNA analysis using the Pyrosequencing technology requires that 45 to 50 PCR cycles are done in order to exhaust all oligonucleotides. Should there be oligonucleotides left, they would interfere in the later steps of Pyrosequencing and produce unreliable data. After 45 to 50 PCR cycles, however, the final quantity of PCR product would not represent the initial copy number of both targeted sequences. Instead, it would be proportional to the quantity of oligonucleotides used to perform the amplification. For the purpose of quantifying the initial copy number, the PCR amplification must be stopped at a stage where the oligonucleotides are not a limiting factor, i.e. during the exponential phase of the amplification. Stopping the PCR amplification during the exponential phase will produce samples where there are remaining oligonucleotides that could interfere with the Pyrosequencing assay. To circumvent this problem, PCR reaction samples are treated, after cycling, to remove any oligonucleotides and single stranded DNA that could be detrimental to the outcome of the experiment. In this example, oligonucleotides and single strand DNA is degraded using Mung bean nuclease.

The next step of this method is to perform the quantification of the co-amplified amplicons. In this experiment, one of the oligonucleotide amplification primers (NPTII-R) is modified and a biotin tag is linked to the most five prime nucleotide. In the same way, one of the oligonucleotides amplification primers (ALS1-R) specific to ALS1 is tagged with biotin. Streptavidin will bind to biotin and using streptavidin coated magnetic beads, it is possible to purify single stranded PCR products from a denaturing solution containing NaOH using a magnet. After a washing step, oligonucleotides extension primers are added to the single stranded DNA template, heated to remove any secondary structure and cooled to allow specific hybridization of the oligonucleotide extension primers to their respective complementary sequence. Two oligonucleotide extension primers are added, one specific to the NPTII amplicon (NPTIIPT) and the other to the ALS1 amplicon (ALS1PT).

The primer extension reaction is performed on the Pyrosequencing PSQ™96 system and extension is monitored in real time. The instrument dispenses nucleotides sequentially and the dispensation order is determined by the user. As described above, it is possible to perform the extension of the extension primers separately. Pyrosequencing technology has the ability to detect the incorporation of each dispensed deoxy-nucleotide by monitoring the emission of light. Such emissions will produce peaks on the Pyrogram (FIG. 3) and these peaks are proportional to the quantity of nucleotides incorporated. Hence, if two amplicons are analyzed in the same Pyrosequencing assay, the average peak height for one amplicon compared to the average of peak height of the second amplicon is indicative of the respective relative quantities.

In this example, the relative quantification of the initial copy number of NPTII is calculated by first averaging peak height values for the five first nucleotides of the dispensation order, specific to NPTII. Peak heights for the next six nucleotides of the dispensation order, specific to ALS1, are also averaged. The NPTII average is divided by the ALS average, resulting in a coefficient representing a relative peak height value average of NPTII, using ALS1 as the reference control.

Figure 3:
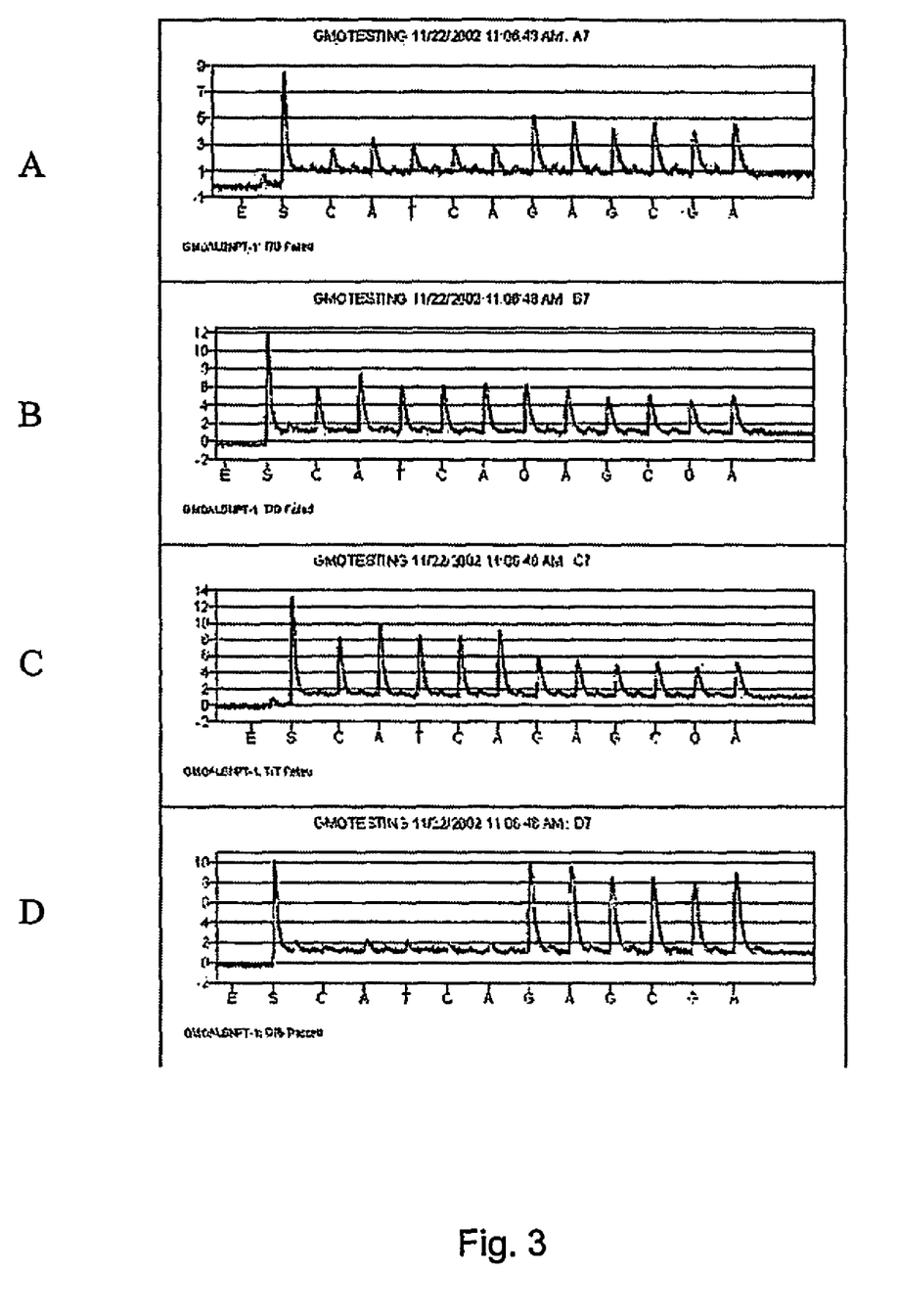
FIG. 3 illustrates pyrosequencing results of the relative quantification of the NPTII transgene in different Canola lines using ALS1 as a control sequence.

FIG. 3 illustrate results obtained in quantifying relative number of copies for the NPTII gene with different-transgenic plants. Genomic DNA extracted from a canola plant carrying a single genomic copy of the NPTII gene, as confirmed by Southern blot analysis (results not shown), is used for duplex PCR amplification and Pyrosequencing analysis. As shown in FIG. 3A, peaks of the same height can be seen when the NPTII amplicon is sequenced, i.e. the first five nucleotides of the dispensation order. At the sixth and for the following nucleotides, specific to ALS1, peaks can also be observed. These latter peaks are of the same height but different from the observed peak heights for the nucleotides specific to NPTII. ALS1 is the control amplicon and its copy number remains the same from sample to sample. In this sample, peak height value from NPTII divided by that for ALS1 is calculated to be 0.52. When genomic DNA coming from a plant bearing two copies of NPTII was submitted to the same analysis (FIG. 3B), the relative intensity of the light pulse from the NPTII nucleotides equals 1.25. Again, genomic DNA of a plant carrying three copies or more of NPTII has a relative value of 1.92 when analyzed in a similar fashion (FIG. 3C). Finally, genomic DNA from a plant in which no copies of NPTII can be found gives a relative value of 0.10 (FIG. 3D). These results are in agreement with what was expected and deduced from previous results obtained through Southern blot hybridizations.

Figure 4:
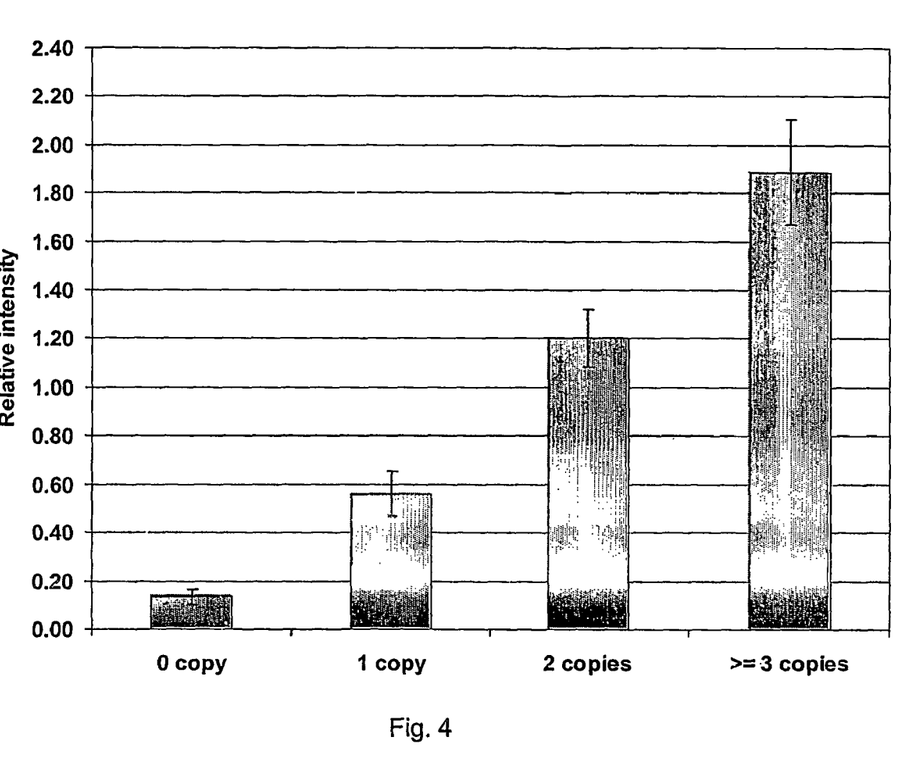
FIG. 4 illustrates a graph showing average relative quantification of replicated experiments and calculated standard deviations. Relative quantification was done for the NPTII transgene in different Canola lines using ALS1 as control sequence.

These experiments were repeated eight times for the genomic DNAs bearing zero and one copy of NPTII and 10 times for the genomic DNAs carrying two and three copies of the transgene (table 1). Relative quantification was done for the NPTII transgene in different Canola lines using ALS1 as control sequence. An average of the relative peak height values and their standard deviation is calculated for each genomic DNA extract. FIG. 4 represents graphically these latter calculations. For each genomic DNA extract, it is clear that the relative peak heights are proportional to the initial copy number. The relative peak height when two copies of the transgene are present in the studied genome is twice as high as the one observed when only one copy of the transgene is present. Similarly, the relative value of genomic DNA bearing at least 3 copies is three times as high as the one obtained when genomic DNA from a plant in which a single integration event took place is analyzed. Finally, little signal is detected when no copies of the transgene are present in the studied genomic DNA. Standard deviations illustrated in FIG. 4 clearly do not overlap when the different genomics extracts are analyzed and hence we conclude that the observed differences are significant.

TABLE 1

Value of peak heights obtained during replicated experiments

| | Nucleotide sequence specific to NPTII | | | | | Nucleotide sequence specific to ALS1 | | | | | Avg. NPTII | Avg. ALS1 | Avg NPTII Avg ALS1 | Avg of rel. values | Std dev |
|---|---|---|---|---|---|---|---|---|---|---|---|---|---|---|---|
| | C | A | T | C | A | G | A | G | C | G | A | | | | | |
| 1 copy of NPTII | 2.4 | 4.4 | 3.1 | 2.7 | 3.1 | 6.3 | 5.2 | 4.4 | 5.1 | 4.8 | 5.2 | 3.14 | 5.17 | 0.607742 | | |
| | 2.4 | 3.9 | 2.6 | 3 | 2.9 | 6.1 | 6 | 4.8 | 5.2 | 4.6 | 5.8 | 2.96 | 5.42 | 0.546462 | | |
| | 1.2 | 1.5 | 1.1 | 1.3 | 1.3 | 2.7 | 2.5 | 2.1 | 2.4 | 2.2 | 2.4 | 1.28 | 2.38 | 0.537063 | | |
| | 2.5 | 3.3 | 2.5 | 2.4 | 2.6 | 4 | 3.4 | 3 | 3.3 | 2.9 | 3.5 | 2.66 | 3.35 | 0.79403 | | |
| | 1.7 | 2.2 | 1.7 | 1.8 | 2 | 4.3 | 4.1 | 3.5 | 3.8 | 3.6 | 3.8 | 1.88 | 3.85 | 0.488312 | | |
| | 1.4 | 1.9 | 1.2 | 1.4 | 1.6 | 3.3 | 2.9 | 2.7 | 2.8 | 2.4 | 2.7 | 1.5 | 2.8 | 0.535714 | | |
| | 2.1 | 3 | 2.1 | 2.1 | 2.3 | 5.5 | 4.9 | 4.4 | 4.8 | 4.4 | 5.1 | 2.32 | 4.85 | 0.478351 | | |
| | 2.1 | 3 | 2.2 | 2.2 | 2.1 | 5.6 | 4.8 | 4.1 | 4.7 | 4.3 | 4.6 | 2.32 | 4.68 | 0.495374 | | |
| | 1.5 | 2.3 | 1.7 | 1.9 | 1.9 | 4.2 | 3.6 | 3.2 | 3.6 | 3 | 3.7 | 1.86 | 3.55 | 0.523944 | | |
| | 1.5 | 2.2 | 1.5 | 1.7 | 1.6 | 3.4 | 2.8 | 2.7 | 2.7 | 2.5 | 2.9 | 1.7 | 2.83 | 0.6 | 0.561 | 0.093 |
| 2 copies of NPTII | 5 | 6.5 | 5.4 | 5 | 5.6 | 5.2 | 4.4 | 3.6 | 4.3 | 3.6 | 4.5 | 5.5 | 4.27 | 1.289063 | | |
| | 4.5 | 6.3 | 4.7 | 4.8 | 5.3 | 5.6 | 4.6 | 4.1 | 5 | 4 | 4.8 | 5.12 | 4.68 | 1.093238 | | |
| | 3.1 | 3.9 | 3 | 2.9 | 3.1 | 3.2 | 2.6 | 2.2 | 2.5 | 2 | 2.5 | 3.2 | 2.5 | 1.28 | | |
| | 4.5 | 5.8 | 4.5 | 4.4 | 4.9 | 4.2 | 3.6 | 3.3 | 3.4 | 3 | 3.6 | 4.82 | 3.52 | 1.370616 | | |
| | 4.1 | 5.2 | 4.1 | 4.2 | 4.6 | 4.8 | 4.1 | 3.7 | 4 | 3.3 | 3.9 | 4.44 | 3.97 | 1.119328 | | |
| | 4.5 | 5.8 | 4.7 | 5 | 5.1 | 4.9 | 4.3 | 3.8 | 4.4 | 3.5 | 4.1 | 5.02 | 4.17 | 1.2048 | | |
| | 3.5 | 4.9 | 3.7 | 3.8 | 4 | 4.3 | 4 | 3.3 | 3.6 | 3.3 | 3.7 | 3.98 | 3.7 | 1.075676 | | |
| | 4.3 | 5.8 | 4.6 | 4.6 | 5.2 | 5.7 | 4.9 | 4.3 | 4.7 | 4.1 | 5.1 | 4.9 | 4.8 | 1.020833 | | |
| | 4.5 | 6.2 | 4.9 | 4.9 | 5 | 5.1 | 4.4 | 3.6 | 4.1 | 3.3 | 3.9 | 5.1 | 4.07 | 1.254098 | | |
| | 4.3 | 5.5 | 4.6 | 4.4 | 4.8 | 4.3 | 3.7 | 3.2 | 3.6 | 3 | 3.7 | 4.72 | 3.58 | 1.317209 | 1.202 | 0.118 |
| ≧3 copies of NPTII | 3.7 | 4.6 | 3.8 | 3.8 | 3.8 | 3.1 | 2.4 | 2 | 2.4 | 1.9 | 2.7 | 3.94 | 2.42 | 1.630345 | | |
| | 5.6 | 7.3 | 5.8 | 5.7 | 6.3 | 3.9 | 3.1 | 2.7 | 3.1 | 2.6 | 3 | 6.14 | 3.07 | 2.002174 | | |
| | 4.9 | 6.3 | 5 | 4.6 | 5.2 | 3.4 | 3.2 | 2.7 | 3.2 | 2.6 | 3.1 | 5.2 | 3.03 | 1.714286 | | |
| | 5.3 | 6.5 | 5.3 | 5.5 | 5.9 | 3.6 | 3 | 2.6 | 2.9 | 2.6 | 2.8 | 5.7 | 2.92 | 1.954286 | | |
| | 8 | 10.3 | 8.4 | 8.6 | 9.2 | 5.7 | 4.7 | 4.1 | 4.7 | 4.2 | 4.8 | 8.9 | 4.7 | 1.893617 | | |
| | 6.5 | 8.3 | 6.5 | 6.3 | 7.2 | 4.8 | 4.2 | 3.8 | 4.4 | 3.7 | 3.9 | 6.96 | 4.13 | 1.683871 | | |
| | 6.9 | 8.7 | 7.2 | 7 | 7.8 | 4.5 | 4.1 | 3.5 | 4.1 | 3.3 | 4 | 7.52 | 3.92 | 1.92 | | |
| | 6.1 | 7.6 | 6.1 | 6.1 | 6.8 | 3.5 | 2.9 | 2.3 | 3 | 2.3 | 3 | 6.54 | 2.83 | 2.308235 | 1.888 | 0.218 |

TABLE 1-continued

Value of peak heights obtained during replicated experiments

| | Nucleotide sequence specific to NPTII | | | | | Nucleotide sequence specific to ALS1 | | | | | | Avg. | Avg. | Avg NPTII Avg | Avg of rel. | Std |
|---|---|---|---|---|---|---|---|---|---|---|---|---|---|---|---|---|
| | C | A | T | C | A | G | A | G | C | G | A | NPTII | ALS1 | ALS1 | values | dev |
| 0 copies of NPTII | 0.8 | 1.2 | 1.1 | 1 | 0.8 | 6.1 | 5.7 | 4.9 | 4.6 | 4.3 | 5.3 | 0.98 | 5.15 | 0.190291 | | |
| | 0.7 | 1.3 | 0.8 | 0.7 | 0.9 | 6.6 | 6.6 | 5.4 | 5.5 | 5.1 | 5.7 | 0.88 | 5.82 | 0.151289 | | |
| | 1 | 1.4 | 1.2 | 0.8 | 0.8 | 7.7 | 7 | 6.2 | 6.4 | 5.9 | 6.6 | 1.04 | 6.63 | 0.156784 | | |
| | 0.5 | 1.4 | 0.9 | 0.7 | 0.9 | 9.4 | 8.8 | 7.6 | 7.4 | 6.8 | 7.6 | 0.88 | 7.93 | 0.110924 | | |
| | 0.3 | 1.3 | 0.9 | 0.9 | 0.8 | 9 | 8.5 | 7.5 | 7.7 | 6.6 | 7.9 | 0.84 | 7.87 | 0.10678 | | |
| | 0.5 | 1 | 0.9 | 0.8 | 0.7 | 8.5 | 8.1 | 7.3 | 7.4 | 6.7 | 7.6 | 0.78 | 7.6 | 0.102632 | | |
| | 0.4 | 1.1 | 0.7 | 0.5 | 0.5 | 6.9 | 6.4 | 5.5 | 5.5 | 5 | 5.5 | 0.64 | 5.8 | 0.110345 | 0.11 | 0.037 |

From these results, it is possible to accurately confirm the number of integrations of a transgene into the genome of different transgenic Canola plants. Furthermore, these results show significant improvements in relative quantification of specific nucleic acid sequences and also illustrate a new application for quantitative measurements of primer extension products.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

The invention claimed is:

1. A method of assessing an amount of a known target nucleic acid sequence in a sample comprising:
   a) co-amplifying using a duplex PCR said known target nucleic acid sequence and a known amount of a known control nucleic acid sequence using different target and control specific primers to produce respective target and control amplicons, wherein said control nucleic acid sequence is different than said target nucleic acid sequence, and wherein said co-amplifying is stopped during an exponential phase of the duplex PCR;
   b) predetermining a dispensation order of nucleotides based on the nucleotide sequence order of the target nucleic acid and control nucleic acid sequence;
   c) dispensing the nucleotides in a single reaction in the predetermined dispensation order in a primer extension reaction such that the target and control nucleic acids are extended sequentially; and
   d) determining relative amounts of said target and control amplicons by
   comparing a quantity of nucleotides incorporated during said primer extension reaction for said target amplicon with a quantity of nucleotides incorporated during said primer extension reaction for said control amplicon, wherein relative amounts of said respective amplicons are proportional to relative quantities of nucleotides incorporated during said primer extension reactions and said amount of said target nucleic acid sequence in said sample is proportional thereto.

2. The method of claim 1, wherein said control nucleic acid is an endogenous or exogenous nucleic acid.

3. The method of claim 1, wherein said primer extension reaction is performed using identical primers for said respective target and control amplicons.

4. The method of claim 1, wherein said primer extension reaction is performed using a different template-specific primer for said respective target and control amplicons.

5. The method of claim 4, wherein said primer extension reaction is detected by detecting pyrophosphate (PPi) release.

6. The method of claim 5, wherein said pyrophosphate is detected luminometrically.

7. The method of claim 6, wherein said pyrophosphate is detected enzymatically using the enzyme luciferase as a PPi-detection enzyme.

8. The method of claim 7, wherein in the primer extension reaction, an a-thio analogue of an adenine nucleotide is used.

9. The method of claim 8, wherein said target nucleic acid and control nucleic acid are co-amplified using amplification primers which are immobilized or carry means for immobilization.

10. The method of claim 9, wherein more than one different control nucleic acid is used.

11. The method of claim 10, wherein different amounts of each different control nucleic acid are used.

12. The method of claim 11, wherein said primer extension reaction is performed on said respective target and control amplicons using identical primers for said respective target and control amplicons.

13. The method of claim 11, wherein said primer extension reaction is performed on said respective target and control amplicons using a different template-specific extension primer on each said amplicon.

14. The method of claim 13, wherein multiple primer extension reactions are performed on each of said respective target or control amplicons.

15. The method of claim 14, wherein each said primer extension reaction yields an extension product of different length or sequence.

16. The method of claim 15, wherein said target nucleic acid is selected from the group consisting of a gene or a fragment thereof, a T-DNA region or a fragment thereof, a vector or a fragment thereof, a plasmid or fragment thereof, a nucleic acid polymorphism and a non-coding region of a nucleic acid sequence.

17. The method of claim 16, wherein said gene or fragment thereof is a gene selected from the group consisting of a disease resistance gene, an antibiotic resistance gene and a gene conferring an investigated trait.

18. A method of assessing copy number of a target nucleic acid sequence in a genome of an organism comprising:
   a) co-amplifying using a duplex PCR said target nucleic acid sequence and a known amount of a known control nucleic acid sequence using different target and control specific primers to produce respective target and control amplicons, wherein said control nucleic acid sequence is different than said target nucleic acid sequence, wherein said co-amplifying is stopped during an exponential phase of the duplex PCR;
   b) predetermining a dispensation order of nucleotides based on the nucleotide sequence order of the target nucleic acid and control nucleic acid sequence;
   c) dispensing the nucleotides in a single reaction in the predetermined dispensation order in a primer extension reaction such that the target and control nucleic acids are extended sequentially; and d) determining relative amounts of said target and control amplicons by comparing a quantity of nucleotides incorporated during said primer extension reaction for said target amplicon with a quantity of nucleotides incorporated during said primer extension reaction for said control amplicon, wherein relative amounts of said respective amplicons are proportional to relative quantities of nucleotides incorporated during said primer extension reactions and copy number of said target nucleic acid sequence in said genome is proportional thereto.

19. The method of claim 18, wherein said control nucleic acid is an endogenous or exogenous nucleic acid.

20. The method of claim 19, wherein said target nucleic acid is selected from the group consisting of a gene or a fragment thereof, a T-DNA region or a fragment thereof, a vector or a fragment thereof, a plasmid or fragment thereof, a nucleic acid polymorphism and a non-coding region of a nucleic acid sequence.

21. The method of claim 20, wherein said gene or fragment thereof is a gene selected from the group consisting of a disease resistance gene, an antibiotic resistance gene, and a gene conferring an investigated trait.

22. A method of assessing copy number of a plasmid in a cell comprising:
   a) co-amplifying using a duplex PCR a target nucleic acid sequence from said plasmid and a known amount of a known control nucleic acid sequence using different target and control specific primers to produce respective target and control amplicons, wherein said control nucleic acid sequence is different than said target nucleic acid sequence, wherein said co-amplifying during an exponential phase of the duplex PCR;
   b) predetermining a dispensation order of nucleotides based on the nucleotide sequence order of the target nucleic acid and control nucleic acid sequence;
   c) dispensing the nucleotides in a single reaction in the predetermined dispensation order in a primer extension reaction such that the target and control nucleic acids are extended sequentially; and
   d) determining relative amounts of said target and control amplicons by comparing a quantity of nucleotides incorporated during said primer extension reaction for said target amplicon with a quantity of nucleotides incorporated during said primer extension reaction for said control amplicon, wherein the relative amounts of said respective amplicons are proportional to the relative quantities of nucleotides incorporated during said primer extension reactions and said copy number of said plasmid in said cell is proportional thereto.

23. The method of claim 21, wherein said control nucleic acid is an endogenous or exogenous nucleic acid.

24. A method of identifying an organism having a single copy of a target nucleic acid sequence comprising:
   a) co-amplifying using a duplex PCR said target nucleic acid sequence and a known amount of a known control nucleic acid sequence using different target and control specific primers to produce respective target and control amplicons, wherein said control nucleic acid sequence is different than said target nucleic acid sequence, wherein said co-amplifying is stopped during an exponential phase of the duplex PCR;
   b) predetermining a dispensation order of nucleotides based on the nucleotide sequence order of the target nucleic acid and control nucleic acid sequence;
   c) dispensing the nucleotides in a single reaction in the predetermined dispensation order in a primer extension reaction such that the target and control nucleic acids are extended sequentially;
   d) determining relative amounts of said target and control amplicons by comparing a quantity of nucleotides incorporated during said primer extension reaction for said target amplicon with a quantity of nucleotides incorporated during said primer extension reaction for said control amplicon, wherein relative amounts of said respective amplicons are proportional to relative quantities of nucleotides incorporated during said primer extension reactions and said copy number of said target nucleic acid sequence is proportional thereto, wherein if a copy number of said target nucleic acid sequence is equal to one, it is indicative of an organism having a single copy of said target nucleic acid sequence.

25. The method of claim 24, wherein said control nucleic acid is an endogenous or exogenous nucleic acid.

26. The method of claim 25, wherein said target nucleic acid is selected from the group consisting of a gene or a fragment thereof, a T-DNA region or a fragment thereof, a vector or a fragment thereof, a plasmid or fragment thereof, a nucleic acid polymorphism and a non-coding region of a nucleic acid sequence.

27. The method of claim 26, wherein said gene or fragment thereof is a gene selected from the group consisting of a disease resistance gene, an antibiotic resistance gene, and a gene conferring an investigated trait.

28. The method of claim 27, wherein said organism is a genetically modified organism.

29. The method of claim 28, wherein said organism is identified from a plurality of organisms.

30. The method of claim 29, wherein said organism is an organism selected from the group consisting of mammals, plants, birds, bacteria, fungi, and viruses.

31. The method of claim 1, wherein said control nucleic acid is acetohydroxyacid synthase (AHAS).

32. The method of claim 1, wherein said target nucleic acid is a chromosome or a fragment thereof and assessing an amount of said target nucleic acid is used to determine chromosome copy number.

33. The method of claim 1, wherein said target nucleic acid is selected from the group consisting of neomycin phosphotransferase (NPTII) phosphinothricin acetyl transferase (PAT), hygromycin phosphotransferase (HPT), acetolactate synthase (ALS, also referred to as acetohydroxyacid synthase (AHAS)), phosphomannose isomerase (PMI), 5-enolpyruvylshikamate-3-phosphate synthase (EPSP synthase), oxalate oxidase, adenosine deaminase, dihydrofolate reductase, thymidine kinase, xanthine-guanine phosphoribosyltransferase, and blasticidin S deaminase.

34. The method of claim 1, wherein said control nucleic acid sequence is selected from the group consisting of acetolactate synthase, actin, profilin, ferredoxin-dependent glutamate synthase, ribose-phosphate pyrophosphokinase, beta-ketoacyl-CoA synthase, delta-5 fatty acid desaturase, sequence-tag sites (STS) of known copy number and non-translated sequences of known copy number.

35. The method of claim 1, wherein said primer extension reaction is performed using a primer specific for NPTII and another primer specific for AHAS.

* * * * *

```
                          SEQUENCE LISTING

<160> NUMBER OF SEQ ID NOS: 9

<210> SEQ ID NO 1
<211> LENGTH: 1600
<212> TYPE: DNA
<213> ORGANISM: Escherichia coli

<400> SEQUENCE: 1
gagctaagca catacgtcag aaaccattat tgcgcgttca aaagtcgcct aaggtcacta        60
tcagctagca aatatttctt gtcaaaaatg ctccactgac gttccataaa ttcccctcgg       120
tatccaatta gagtctcata ttcactctca atccaaataa tctgcaccgg atctggatcg       180
tttcgcatga ttgaacaaga tggattgcac gcaggttctc cggccgcttg ggtggagagg       240
ctattcggct atgactgggc acaacagaca atcggctgct ctgatgccgc cgtgttccgg       300
ctgtcagcgc aggggcgccc ggttcttttt gtcaagaccg acctgtccgg tgccctgaat       360
gaactgcagg acgaggcagc gcggctatcg tggctggcca cgacgggcgt tccttgcgca       420
gctgtgctcg acgttgtcac tgaagcggga agggactggc tgctattggg cgaagtgccg       480
gggcaggatc tcctgtcatc tcaccttgct cctgccgaga aagtatccat catggctgat       540
gcaatgcggc ggctgcatac gcttgatccg gctacctgcc cattcgacca ccaagcgaaa       600
catcgcatcg agcgagcacg tactcggatg aagccggtc ttgtcgatca ggatgatctg       660
gacgaagagc atcaggggct cgcgccagcc gaactgttcg ccaggctcaa ggcgcgcatg       720
cccgacggcg atgatctcgt cgtgacccat ggcgatgcct gcttgccgaa tatcatggtg       780
gaaaatggcc gcttttctgg attcatcgac tgtggccggc tgggtgtggc ggaccgctat       840
caggacatag cgttggctac ccgtgatatt gctgaagagc ttggcggcga atgggctgac       900
cgcttcctcg tgctttacgg tatcgccgct cccgattcgc agcgcatcgc cttctatcgc       960
cttcttgacg agttcttctg agcgggactc tggggttcga aatgaccgac caagcgacgc      1020
```

```
ccaacctgcc atcacgagat ttcgattcca ccgccgcctt ctatgaaagg ttgggcttcg    1080
gaatcgtttt ccgggacgcc ggctggatga tcctccagcg cggggatctc atgctggagt    1140
tcttcgccca cggatctct gcggaacagg cggtcgaagg tgccgatatc attacgacag    1200
caacggccga caagcacaac gccacgatcc tgagcgacaa tatgatcggg cccggcgtcc    1260
acatcaacgg cgtcggcggc gactgcccag gcaagaccga gatgcaccgc gatatcttgc    1320
tgcgttcgga tattttcgtg gagttcccgc cacagacccg gatgatcccc gatcgttcaa    1380
acatttggca ataaagtttc ttaagattga atcctgttgc cggtcttgcg atgattatca    1440
tataatttct gttgaattac gttaagcatg taataattaa catgtaatgc atgacgttat    1500
ttatgagatg ggttttatg attagagtcc cgcaattata catttaatac gcgatagaaa    1560
acaaaatata gcgcgcaaac taggataaat tatcgcgcgc                         1600

<210> SEQ ID NO 2
<211> LENGTH: 1574
<212> TYPE: DNA
<213> ORGANISM: Brassica napus

<400> SEQUENCE: 2
gacataccta ggatcgttca agaagctttc tttctagcta cttccggtag acccggaccg      60
gttttggttg atgttcctaa ggatattcag cagcagcttg cgattcctaa ctgggatcaa     120
cctatgcgct tacctggcta catgtctagg ttgcctcagc ctccggaagt ttctcagtta     180
ggtcagatcg ttaggttgat ctcggagtct aagaggcctt ttttgtacgt tggtggtgga     240
agcttgaact cgagtgaaga actggggaga tttgtcgagc ttactgggat ccccgttgcg     300
agtactttga tggggcttgg ctcttatcct tgtaacgatg agttgtccct gcagatgctt     360
ggcatgcacg ggactgtgta tgctaactac gctgtggagc atagtgattt gttgctggcg     420
tttggtgtta ggtttgatga ccgtgtcacg ggaaagctcg aggctttcgc tagcagggct     480
aaaattgtgc acatagacat tgattctgct gagattggga agaataagac acctcacgtg     540
tctgtgtgtg tgatgtaaa gctggctttg caagggatga caaggttct tgagaaccgg     600 gcggaggagc tcaagcttga tttcggtgtt tggaggagtg agttgagcga gcagaaacag     660 aagttcccctt tgagcttcaa aacgtttgga gaagccattc ctccgcagta cgcgattcag     720
atcctcgacg agctaaccga agggaaggca attatcagta ctggtgttgg acagcatcag     780
atgtgggcgg cgcagtttta caagtacagg aagccgagac agtggctgtc gtcatcaggc     840
ctcggagcta tgggttttgg acttcctgct gcgattggag cgtctgtggc gaaccctgat     900
gcgattgttg tggatattga cggtgatgga agcttcataa tgaacgttca agagctggcc     960
acaatccgtg tagagaatct tcctgtgaag atactcttgt taaacaacca gcatcttggg    1020
atggtcatgc aatgggaaga tcggttctac aaagctaaca gagctcacac ttatctcggg    1080
gacccggcaa gggagaacga gatcttccct aacatgctgc agtttgcagg agcttgcggg    1140
attccagctg cgagagtgac gaagaaagaa gaactccgag aagctattca gacaatgctg    1200
gatacaccag gaccataacct gttggatgtg atatgtccgc accaagaaca tgtgttaccg    1260
atgatcccaa gtggtggcac tttcaaagat gtaataacag aaggggatgg tcgcactaag    1320
tactgagaga tgaagctggt gatcgatcat atggtaaaag acttagtttc agtttccagt    1380 ttctttttgtg tggtaatttg ggtttgtcag ttgttgtact acttttggtt gttcccagac    1440
gtactcgctg ttgttgtttt gtttccttttt tcttttatat ataaataaac tgcttgggtt    1500
```

-continued

```
tttttttcata tgtttgggac tcaatgcaag gaatgctact agactgcgat tatctactaa    1560
tcttgctagg aaat                                                      1574
```

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3

```
cagctgtgct cgacgttgtc a                                                21
```

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4

```
gccatgggtc acgacgagat                                                  20
```

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5

```
ggaaagctcg aggctttcgc t                                                21
```

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

```
gccgcccaca tctgatgctg t                                                21
```

<210> SEQ ID NO 7
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

```
tttggaggag tgagtt                                                      16
```

<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

```
ctgccgagaa agtatc                                                    16

<210> SEQ ID NO 9
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
catcagagcg a                                                         11
```